United States Patent
Hwang et al.

(10) Patent No.: US 10,653,812 B2
(45) Date of Patent: May 19, 2020

(54) METHOD OF PREPARING SUPERABSORBENT POLYMER

(71) Applicant: LG Chem, Ltd., Seoul (KR)

(72) Inventors: Min Ho Hwang, Daejeon (KR); Hye Mi Nam, Daejeon (KR); Sang Gi Lee, Daejeon (KR); Soo Jin Lee, Daejeon (KR); Tae Hwan Jang, Daejeon (KR)

(73) Assignee: LG Chem, Ltd. (KR)

( * ) Notice: Subject to any disclaimer, the term of this patent is extended or adjusted under 35 U.S.C. 154(b) by 151 days.

(21) Appl. No.: 15/755,340

(22) PCT Filed: Jun. 13, 2016

(86) PCT No.: PCT/KR2016/006263
§ 371 (c)(1),
(2) Date: Feb. 26, 2018

(87) PCT Pub. No.: WO2017/164459
PCT Pub. Date: Sep. 28, 2017

(65) Prior Publication Data
US 2018/0243464 A1 Aug. 30, 2018

(30) Foreign Application Priority Data

Mar. 25, 2016 (KR) .......................... 10-2016-0036380

(51) Int. Cl.

| | | |
|---|---|---|
| *A61L 15/60* | (2006.01) | |
| *B01J 20/26* | (2006.01) | |
| *B01J 20/08* | (2006.01) | |
| *B01J 20/30* | (2006.01) | |
| *A61L 15/24* | (2006.01) | |
| *C08J 3/24* | (2006.01) | |
| *C08J 3/12* | (2006.01) | |
| *C08K 5/151* | (2006.01) | |
| *C08L 33/00* | (2006.01) | |
| *C08J 3/075* | (2006.01) | |
| *C08K 3/22* | (2006.01) | |
| *B01J 20/28* | (2006.01) | |

(52) U.S. Cl.
CPC .............. *A61L 15/60* (2013.01); *A61L 15/24* (2013.01); *B01J 20/08* (2013.01); *B01J 20/267* (2013.01); *B01J 20/28004* (2013.01); *B01J 20/28026* (2013.01); *B01J 20/3021* (2013.01); *B01J 20/3085* (2013.01); *C08J 3/075* (2013.01); *C08J 3/12* (2013.01); *C08J 3/24* (2013.01); *C08K 3/22* (2013.01); *C08K 5/151* (2013.01); *C08L 33/00* (2013.01); *C08J 2300/12* (2013.01)

(58) Field of Classification Search
None
See application file for complete search history.

(56) References Cited

U.S. PATENT DOCUMENTS

| | | |
|---|---|---|
| 5,164,459 A | 11/1992 | Kimura et al. |
| 5,419,956 A | 5/1995 | Roe |
| 6,124,391 A | 9/2000 | Sun et al. |
| 8,420,567 B1 | 4/2013 | Naumann et al. |
| 9,440,220 B2 | 9/2016 | Naumann et al. |
| 9,700,871 B2 | 7/2017 | Lee et al. |
| 2004/0214946 A1* | 10/2004 | Smith ..................... A61L 15/60 524/556 |
| 2008/0306209 A1* | 12/2008 | Stueven ................... C08F 2/44 524/706 |
| 2010/0119312 A1 | 5/2010 | Nagashima et al. |
| 2012/0035294 A1 | 2/2012 | Kim et al. |
| 2013/0172180 A1 | 7/2013 | Naumann et al. |
| 2015/0225514 A1 | 8/2015 | Kimura et al. |
| 2015/0360204 A1 | 12/2015 | Tachi et al. |
| 2016/0053037 A1 | 2/2016 | Lee et al. |
| 2016/0151531 A1 | 6/2016 | Lee et al. |

(Continued)

FOREIGN PATENT DOCUMENTS

| | | |
|---|---|---|
| CN | 101389661 A | 3/2009 |
| CN | 102702418 A | 10/2012 |

(Continued)

OTHER PUBLICATIONS

International Search Report for PCT/KR2016/006263 dated Jan. 13, 2017.
Extended European Search Report including Written Opinion for Application No. EP16895585.4 dated Jun. 25, 2018.
Chinese Search Report for Application No. 201680050459.X, dated Mar. 13, 2020, pp. 1-3.

*Primary Examiner* — Jospeph D Anthony
(74) *Attorney, Agent, or Firm* — Lerner, David, Littenberg, Krumholz & Mentlik, LLP

(57) ABSTRACT

Provided is a method of preparing a superabsorbent polymer which exhibits more improved liquid permeability and absorption rate while maintaining excellent absorption performance. The method of preparing the superabsorbent polymer may include the steps of: performing crosslinking polymerization of water-soluble ethylene-based unsaturated monomers having acidic groups which are at least partially neutralized in the presence of an internal crosslinking agent to form a water-containing gel polymer including a crosslinked polymer; drying, pulverizing, and size-sorting the water-containing gel polymer to form a base polymer powder; performing surface-crosslinking of the base polymer powder using a surface-crosslinking solution including one or more surface-crosslinking agents in the presence of first alumina particles; and adding second alumina particles to the surface-crosslinked base polymer powder and then mixing them with each other.

12 Claims, No Drawings

(56) References Cited

U.S. PATENT DOCUMENTS

| | | |
|---|---|---|
| 2016/0214082 A1 | 7/2016 | Lee et al. |
| 2016/0271584 A1 | 9/2016 | Lee et al. |
| 2017/0073478 A1 | 3/2017 | Joo et al. |
| 2018/0147557 A1* | 5/2018 | Hwang ................ B01J 20/3085 |

FOREIGN PATENT DOCUMENTS

| | | |
|---|---|---|
| CN | 104024291 A | 9/2014 |
| CN | 105209524 A | 12/2015 |
| CN | 105392805 A | 3/2016 |
| EP | 3279241 A1 | 2/2018 |
| JP | 2002226599 A | 8/2002 |
| JP | 4199679 B2 | 12/2008 |
| JP | 5601495 B2 | 10/2014 |
| JP | 5611523 B2 | 10/2014 |
| KR | 0143403 B1 | 7/1998 |
| KR | 19990027352 A | 4/1999 |
| KR | 20010072728 A | 7/2001 |
| KR | 100873455 B1 | 12/2008 |
| KR | 20130018350 A | 2/2013 |
| KR | 20140107491 A | 9/2014 |
| KR | 20140144259 A | 12/2014 |
| KR | 101507287 B1 | 3/2015 |
| KR | 20150056572 A | 5/2015 |
| KR | 20150064649 A | 6/2015 |
| KR | 20150064712 A | 6/2015 |
| KR | 20160004967 A | 1/2016 |
| KR | 20160016714 A | 2/2016 |

* cited by examiner

METHOD OF PREPARING SUPERABSORBENT POLYMER

CROSS-REFERENCE TO RELATED APPLICATIONS

The present application is a national phase entry under 35 U.S.C. § 371 of International Application No. PCT/KR2016/006263, filed on Jun. 13, 2016, which claims priority from Korean Patent Application No. 10-2016-0036380, filed on Mar. 25, 2016, the disclosures of which inure hereby incorporated by reference.

TECHNICAL FIELD

The present invention relates to a method of preparing a superabsorbent polymer which exhibits more improved liquid permeability and absorption rate while maintaining excellent absorption performance.

BACKGROUND OF THE INVENTION

A superabsorbent polymer (SAP) is a synthetic polymeric material capable of absorbing moisture from about 500 to 1000 times its own weight. Various manufacturers have given it different names, such as a SAM (Super Absorbency Material), an AGM (Absorbent Gel Material), etc. Such superabsorbent polymers started to be practically applied in sanitary products, and now they are widely used not only for hygiene products such as disposable diapers for children, etc., but also for water retaining soil products for gardening, water stop materials for civil engineering and construction, sheets for raising seedling, fresh-keeping agents for food distribution fields, materials for poultices, etc.

In most cases, these superabsorbent polymers have been widely used in the field of hygienic materials such as diapers, sanitary napkins, etc. For these applications, superabsorbent polymers are required to exhibit a high absorption rate with respect to water, etc., must not release absorbed water even under external pressure, and also must maintain their shape under volume expansion (swelling) after water absorption to show excellent permeability.

Recently, as efforts have been made to provide diapers which are thinner and lighter while showing excellent performance, much attention is focused on superabsorbent polymers having more improved liquid permeability and absorption rate. In order to achieve such high absorption rate and improved liquid permeability, a superabsorbent polymer particle, particularly, a surface-crosslinked layer, must have higher surface strength to show high gel strength, which allows urine to be uniformly and rapidly distributed into an absorbent core of a diaper.

However, in the case of increasing gel strength and improving liquid permeability and absorption rate by using the previously known methods, there is a disadvantage that basic absorption performance (absorption amount under no load and under a load) is greatly reduced.

Accordingly, there is a continuous demand for technologies capable of providing superabsorbent polymers having more improved liquid permeability and absorption rate while maintaining excellent basic absorption performance.

DETAILS OF THE INVENTION

Objects of the Invention

The present invention relates to a method of preparing a superabsorbent polymer which exhibits more improved liquid permeability and absorption rate while maintaining excellent absorption performance.

Means for Achieving the Object

According to an embodiment of the present invention, a method of preparing a superabsorbent polymer is provided, the method including the steps of: performing crosslinking polymerization of water-soluble ethylene-based unsaturated monomers having acidic groups which are at least partially neutralized in the presence of an internal crosslinking agent to form a water-containing gel polymer containing a cross-linked polymer; drying, pulverizing, and size-sorting the water-containing gel polymer to form a base polymer powder; performing surface-crosslinking of the base polymer powder using a surface-crosslinking solution including one or more surface-crosslinking agents selected from the group consisting of an alkylene carbonate having 2 to 5 carbon atoms, diol, triol, or polyol containing an alkyl group having 2 to 12 carbon atoms or polyethylene glycol having 2 to 12 carbon atoms, and diepoxy, triepoxy, or polyepoxy containing an alkyl group having 2 to 12 carbon atoms or polyethylene glycol having 2 to 12 carbon atoms, in the presence of first alumina particles; and adding second alumina particles to the surface-crosslinked base polymer powder and then mixing them with each other.

The surface-crosslinking step may include the step of surface-crosslinking the base polymer powder by heat treatment in the presence of the surface-crosslinking solution including the first alumina particles and the surface-crosslinking agent. Further, the surface-crosslinking step may include the steps of: treating the base polymer powder with the first alumina particles in a solid state; and surface-crosslinking the base polymer powder by heat treatment in the presence of the surface-crosslinking solution including the surface-crosslinking agent.

In the present invention, the first alumina particles may have a water contact angle of 10° to 150°. Further, the first alumina particles may be used in an amount of 0.001 to 1.0 parts by weight with respect to 100 parts by weight of the base polymer.

The water-soluble ethylene-based unsaturated monomer may include: one or more selected from the group consisting of an anionic monomer or salts thereof, a nonionic hydrophilic monomer, and an amino group-containing unsaturated monomer or a quaternary compound thereof, and in which the anionic monomer is acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid; the nonionic hydrophilic monomer is (meth)acrylamide, N-substituted (meth)acrylate, 2-hydroxyethyl(meth)acrylate, 2-hydroxypropyl(meth)acrylate, methoxy polyethylene glycol (meth)acrylate, or polyethylene glycol (meth)acrylate; and the amino group-containing unsaturated monomer is (N,N)-dimethylaminoethyl(meth)acrylate or (N,N)-dimethylaminopropyl(meth)acrylate.

The internal crosslinking agent may include one or more selected from the group consisting of bis(meth)acrylamide containing an alkyl group having 2 to 12 carbon atoms or polyethylene glycol having 2 to 12 carbon atoms, poly(meth)acrylate of polyol containing an alkyl group having 2 to 12 carbon atoms or polyethylene glycol having 2 to 12 carbon atoms, and a poly(meth)allyl ether of polyol containing an alkyl group having 2 to 12 carbon atoms or polyethylene glycol having 2 to 12 carbon atoms.

In the present invention, the base polymer powder may be pulverized and size-sorted such that it has a particle size of 150 μm to 850 μm.

The surface-crosslinking step may be performed by heat treatment by raising an initial temperature of 20° C. to 130° C. to a maximum temperature of 140° C. to 200° C. for 10 min to 30 min, and maintaining the maximum temperature for 5 min to 60 min.

Meanwhile, the second alumina particles may have a water contact angle of 10° to 150°. The second alumina particles may be used in an amount of 0.05 to 0.5 parts by weight with respect to 100 parts by weight of the surface-crosslinked superabsorbent polymer.

Mixing of the second alumina particles may be performed at a speed of 100 to 3000 rpm for 2 s to 3 min.

Effects of the Invention

According to the present invention, a superabsorbent polymer having more improved liquid permeability and absorption rate while maintaining excellent absorption performance such as centrifuge retention capacity, absorbency under pressure, etc. Is manufactured and provided.

Such a superabsorbent polymer may be suitably applied to hygiene products such as diapers, and particularly, ultra-thin hygiene products with reduced pulp content.

DETAILED DESCRIPTION OF THE EMBODIMENTS

The terms "first", "second", and the like may be used herein to describe various elements, but are only used to distinguish one element from another.

The terminology used herein is for the purpose of describing exemplary embodiments only and is not intended to limit the present disclosure.

The singular forms used herein may be intended to include the plural forms as well, unless the context clearly indicates otherwise.

It will be understood that the terms "comprise", "include", "equip", and "have" when used herein specify the presence of stated features, integers, steps, elements (components), or combinations thereof, but do not preclude the presence or addition of one or more other features, integers, steps, elements (components), or combinations thereof. While the present invention is susceptible to various modifications and alternative forms, specific exemplary embodiments will be illustrated and described in detail as follows.

It should be understood, however, that the description is not intended to limit the present invention to the particular forms disclosed, but on the contrary, the intention is to cover all modifications, equivalents, and alternatives falling within the spirit and scope of the invention.

Hereinafter, a method of preparing a superabsorbent polymer according to a preferred embodiment of the present invention will be described in more detail.

According to an embodiment of the present invention, a method of preparing a superabsorbent polymer is provided, the method including the steps of: performing crosslinking polymerization of water-soluble ethylene-based unsaturated monomers having acidic groups which are at least partially neutralized in the presence of an internal crosslinking agent to form a water-containing gel polymer containing a crosslinked polymer; drying, pulverizing, and size-sorting the water-containing gel polymer to form a base polymer powder; performing surface-crosslinking of the base polymer powder using a surface-crosslinking solution including one or more surface-crosslinking agents selected from the group consisting of an alkylene carbonate having 2 to 5 carbon atoms, diol, triol, or polyol containing an alkyl group having 2 to 12 carbon atoms or polyethylene glycol having 2 to 12 carbon atoms, and diepoxy, triepoxy, or polyepoxy containing an alkyl group having 2 to 12 carbon atoms or polyethylene glycol having 2 to 12 carbon atoms, in the presence of first alumina particles; and adding second alumina particles to the surface-crosslinked base polymer powder and then mixing them with each other.

The present inventors studied to further improve liquid permeability and absorption rate of a superabsorbent polymer, and as a result, they found that when conditions of a preparation process of the superabsorbent polymer, for example, a kind and a content of an internal crosslinking agent to be described later and polymerization conditions are optimized to obtain a base polymer powder having high gel strength, and particular conditions at the time of surface-crosslinking and immediately after surface-crosslinking (e.g., use of specific alumina particles at the time of surface-crosslinking and immediately after surface-crosslinking) are applied, a superabsorbent polymer maintaining excellent absorption performance (absorption amount under no load and under a load; CRC, GBP, and vortex described below) while showing greatly improved liquid permeability and absorption rate, compared to those previously known, may be provided.

Particularly, it seems that when the first alumina particles defined by a predetermined range of contact angle are used at the time of surface-crosslinking and the surface-crosslinking is performed under a predetermined temperature elevation condition, the surface-crosslinked layer having a thickness above a predetermined level may be uniformly formed on the base polymer powder having high gel strength. It is likely that this is because not only are the first alumina particles uniformly included in the crosslinked structure of the surface-crosslinked layer to make the crosslinked structure more rigid, but also the surface-crosslinking reaction appropriately takes place around the first alumina particles under the above-temperature elevation condition at the time of surface-crosslinking to form the appropriate crosslinked structure.

In addition, surface treatment of the surface-crosslinked superabsorbent polymer with the second alumina particles defined by a predetermined range of contact angle may be performed to effectively prevent direct agglomeration of superabsorbent polymer particles, to improve liquid permeability, and to maintain excellent absorption properties of the superabsorbent polymer.

In general, it is known that when alumina is used in surface-treatment, efficiency of liquid permeability may be relatively reduced, and when alumina is added after surface-treatment, reduction of absorbency under load may increase and separation of alumina from the surface of the superabsorbent polymer may occur during packaging, storage, transportation, etc. To cause deterioration of physical properties. Accordingly, in the present invention, the first alumina particles and the second alumina particles are used in surface treatment, respectively, thereby improving liquid permeability and preventing agglomeration, or maintaining excellent absorbency under load while improving the absorption rate.

Further, since the surface-crosslinked layer may further increase gel strength of the respective superabsorbent polymer particles, the superabsorbent polymer of an embodiment may exhibit high gel strength, and greatly improved absorption performance under load and liquid permeability (GBP) which are supported by examples described below, thereby showing improved absorption rate. Further, as the internal crosslinked structure and the surface crosslinked structure of the superabsorbent polymer prepared by the method of an embodiment are optimized, the superabsorbent polymer may maintain excellent absorption performance such as relatively high absorption rate (vortex) and centrifuge retention capacity (CRC).

Therefore, since the superabsorbent polymer of an embodiment may exhibit excellent absorption performance, together with greatly improved liquid permeability and absorption rate, compared to those previously known, it may be very desirably applied to a variety of hygiene products such as ultra-thin diapers with reduced pulp content.

Hereinafter, the method of preparing the superabsorbent polymer of an embodiment will be described in more detail.

A superabsorbent polymer may be generally prepared by polymerizing water-soluble ethylene-based unsaturated monomers having acidic groups which are at least partially neutralized, for example, acrylic acid having carboxylic acids which are at least partially neutralized in a sodium salt or a mixture of sodium salts thereof, in the presence of an internal crosslinking agent, and then by performing drying, pulverizing, size-sorting, and surface-crosslinking. Specifically, in the preparation method of an embodiment, the superabsorbent polymer may be obtained by performing crosslinking polymerization of the monomers in the presence of the internal crosslinking agent to obtain a base polymer powder, and then surface-crosslinking the base polymer powder in the presence of a predetermined surface-crosslinking agent and first alumina particles.

Particularly, it was confirmed that when a kind and a content of the internal crosslinking agent and polymerization conditions are controlled to obtain a base polymer powder having high gel strength, and surface-crosslinking is performed, for example, by using the specific first alumina particles, and then the surface-crosslinked polymer is treated with the specific second alumina particles, the superabsorbent polymer having the above-described excellent physical properties and effects may be prepared. The preparation method of an embodiment is characterized by using first and second alumina particles as described below at the time of surface-crosslinking and immediately after surface-crosslinking. For example, in the present invention, a wet method of using a surface-crosslinking solution including the first alumina particles at the time of surface-crosslinking and a dry method of treating the second alumina particles after surface-crosslinking are employed at the same time, thereby improving liquid permeability and preventing agglomeration, or obtaining excellent absorbency under load while improving the absorption rate.

First, in the preparation method according to an embodiment, the first alumina particles having a water contact angle of more than 10°, more than 10° and 150° or less, or more suitably, 12° to 150°, may be used at the time of surface-crosslinking. Thus, the superabsorbent polymer prepared by the preparation method according to an embodiment may further include the first alumina particles dispersed on the surface of the base polymer powder, for example, on the surface-crosslinked layer.

More specifically, the first alumina particles may be treated after being included in the surface-crosslinking solution, or the first alumina particles may be mixed in a solid state with the base polymer powder before surface-crosslinking, as described in more detail below. Therefore, at least part of the first alumina particles may exist on the surface of the base polymer powder, for example, on the surface-crosslinked layer, and the rest thereof may be embedded in the surface of the base polymer powder or embedded inside the base polymer powder. Further, the hydrophilic alumina particles may be dispersed on the surface-crosslinked layer to exist in the crosslinked structure included therein.

As the alumina particles for the improvement of liquid permeability exist at least in the surface-crosslinked layer, excellent physical properties, such as liquid permeability or absorption rate improved thereby, may be manifested and maintained for a long period of time.

As the first alumina particles, one or more kinds of commercially available alumina particles having a contact angle of the above range may be used without limitation. More suitably, when the first alumina particles are used after being included in the surface-crosslinking solution, particles having a contact angle of more than 10° and 50° or less may be used in terms of dispersibility in the surface-crosslinking solution, or particles having a contact angle of 50° to 150° or less may be used, together with a separate dispersing agent.

When the first alumina particles in a solid state are added to and mixed with the base polymer powder for dry treatment before surface-crosslinking, particles having a contact angle of 50° to 150° or less may be more preferably used in terms of more effective improvement of liquid permeability and absorption rate.

More specifically, alumina particles under the trade names of Aeroxide Alu 65, Aeroxide Alu C, Aeroxide Alu 130, etc. May be suitably used as the alumina particles to further improve liquid permeability or absorption rate of the superabsorbent polymer.

The water contact angle of the alumina particles may be defined by a water contact angle of each alumina particle which is measured on a glass substrate.

Meanwhile, in the method of preparing the superabsorbent polymer according to an embodiment, the water-soluble ethylene-based unsaturated monomer may include one or more selected from the group consisting of an anionic monomer such as acrylic acid, (meth)acrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl (meth)acrylate, 2-hydroxypropyl(meth)acrylate, methoxy polyethylene glycol (meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylamide, and a quaternary compound thereof. Among them, acrylic acid or salts thereof, for example, acrylic acid which is at least partially neutralized, and/or alkali metal salts thereof such as sodium salts thereof may be used, and it is possible to prepare the superabsorbent polymer having superior physical properties by using these monomers. When acrylic acid and the alkali metal salt thereof are used as the monomer, acrylic acid may be used after neutralizing at least part thereof with a basic compound such as caustic soda (NaOH).

Further, as the internal crosslinking agent for crosslinking polymerization of the monomer, one or more selected from the group consisting of bis(meth)acrylamide including an alkyl group having 2 to 12 carbon atoms, polyethylene glycol having 2 to 12 carbon atoms, etc., poly(meth)acrylate of polyols including an alkyl group having 2 to 12 carbon atoms, polyethylene glycol having 2 to 12 carbon atoms, etc., and poly(meth)allyl ether of polyols including an alkyl group having 2 to 12 carbon atoms, polyethylene glycol having 2 to 12 carbon atoms, etc., may be used. More specifically, as the internal crosslinking agent, one or more poly(meth)acrylates of polyols selected from the group consisting of polyethylene glycol di(meth)acrylate, polypropylene glycol di(meth)acrylate, glycerin diacrylate, glycerin triacrylate, and trimethylol triacrylate may be suitably used. Among them, by using the internal crosslinking agent such as polyethylene glycol di(meth)acrylate, etc., the base polymer powder having high gel strength, wherein the internal crosslinked structure is optimized, may be obtained, whereby the superabsorbent polymer satisfying excellent physical properties may be more suitably obtained.

Further, the specific internal crosslinking agent may be used in a ratio of about 0.005 mol or more, about 0.005 mol to 0.1 mol, or about 0.005 mol to 0.05 mol (or about 0.3 parts by weight or more, or 0.3 to 0.6 parts by weight relative to 100 parts by weight of acrylic acid), based on 1 mol of non-neutralized acrylic acid contained in the monomer. According to the range of the content of the internal crosslinking agent, the base polymer powder having high gel strength before surface-crosslinking may be suitably obtained, and the superabsorbent polymer having excellent physical properties may be obtained by the method of an embodiment.

After performing crosslinking polymerization of the monomers by using the internal crosslinking agent, processes such as drying, pulverizing, and size-sorting may be performed to obtain the base polymer powder. Through the pulverizing and size-sorting processes, the base polymer powder and the superabsorbent polymer obtained therefrom are suitably prepared and provided such that they have a particle size of about 150 µm to 850 µm. More specifically, at least about 95% by weight of the base polymer powder and the superabsorbent polymer obtained therefrom have a particle size of about 150 µm to 850 µm, and the amount of fine particles having a particle size of less than 150 µm may be less than 3% by weight, or less than about 1.5% by weight.

By adjusting the particle size distribution of the base polymer powder and the superabsorbent polymer within the preferred range, the superabsorbent polymer may more suitably exhibit the excellent physical properties mentioned above.

Respective steps of the above-described method of an embodiment will be described in more detail below. However, with regard to the above-mentioned monomer, internal crosslinking agent, alumina particles, and particle size distribution, duplicated explanation thereof will be omitted, and the remaining process configurations and conditions will be described according to each step of the process.

The method of preparing the superabsorbent polymer may include the steps of: performing thermal polymerization photo-polymerization of a monomer composition including a water-soluble ethylene-based unsaturated monomer, an internal crosslinking agent, and a polymerization initiator to form a water-containing gel polymer containing a crosslinked polymer; drying the water-containing gel polymer; pulverizing and size-sorting the dried polymer to form a base polymer; performing surface-crosslinking of the base polymer powder using a surface-crosslinking solution including one or more surface-crosslinking agents selected from the group consisting of an alkylene carbonate having 2 to 5 carbon atoms, diol, triol, or polyol containing an alkyl group having 2 to 12 carbon atoms or polyethylene glycol having 2 to 12 carbon atoms, and diepoxy, triepoxy, or polyepoxy containing an alkyl group having 2 to 12 carbon atoms or polyethylene glycol having 2 to 12 carbon atoms, in the presence of first alumina particles; and adding second alumina particles to the surface-crosslinked base polymer powder and then mixing them with each other.

With regard to the preparation method, the monomer composition includes the water-soluble ethylene-based unsaturated monomer, the internal crosslinking agent, and the polymerization initiator, and a kind of the monomer is the same as described above.

In the above composition, a concentration of the water-soluble ethylene-based unsaturated monomer may be 20% by weight to 60% by weight, or 40% by weight to 50% by weight with respect to the entire monomer composition including the above-described raw materials and a solvent, and it may be suitably controlled in consideration of a polymerization time, reaction conditions, or the like. However, if the concentration of the monomer is too low, the yield of the superabsorbent polymer may become low, and economical problems may occur. On the contrary, if the concentration of the monomer is too high, there is a process problem that a part of the monomers is precipitated or pulverization efficiency of the polymerized water-containing gel polymer is lowered, and the physical properties of the superabsorbent polymer may be deteriorated.

Further, the polymerization initiator is not particularly limited as long as it is generally used in the preparation of the superabsorbent polymer.

Specifically, the polymerization initiator may include a thermal polymerization initiator or a photo-polymerization initiator by UV irradiation, according to the polymerization method. However, even in the case of the photo-polymerization method, a thermal polymerization initiator may be additionally included because a certain amount of heat is generated by the irradiation of UV rays or the like and a certain amount of heat is generated according to the progress of the exothermic polymerization reaction.

The photo-polymerization initiator may be used without limitation in the constitution as long as it is a compound which may form a radical by light such as UV rays.

As the photo-polymerization initiator, for example, one or more selected from the group consisting of benzoin ether, dialkyl acetophenone, hydroxyl alkylketone, phenyl glyoxylate, benzyl dimethyl ketal, acyl phosphine, and α-aminoketone may be used. As the specific example of the acyl phosphine, commercialized Lucirin TPO, namely, 2,4,6-trimethyl-benzoyl-trimethyl phosphine oxide, may be used. More various photo-polymerization initiators are well disclosed in "UV Coatings: Basics, Recent Developments and New Application" written by Reinhold Schwalm, (Elsevier, 2007), p 115, however the example of the photo-polymerization initiator is not limited thereto.

The photo-polymerization initiator may be included at a concentration of about 0.01% by weight to about 1.0% by weight based on the monomer composition. When the concentration of the photo-polymerization initiator is too low, a polymerization rate may become slow, and when the concentration of the photo-polymerization initiator is too high, a molecular weight of the superabsorbent polymer may become small and the physical properties may become uneven.

Further, as the thermal polymerization initiator, one or more selected from the group consisting of a persulfate-based initiator, an azo-based initiator, hydrogen peroxide, and ascorbic acid may be used. Specific examples of the persulfate-based initiator may include sodium persulfate ($Na_2S_2O_8$), potassium persulfate ($K_2S_2O_8$), ammonium persulfate (($NH_4)_2S_2O_8$), etc.; and examples of the azo-based initiator may include 2,2-azobis(2-amidinopropane)dihydrochloride, 2,2-azobis-(N,N-dimethylene)isobutyramidine dihydrochloride, 2-(carbamoylazo)isobutyronitrile, 2,2-azobis[2-(2-imidazolin-2-yl)propane]dihydrochloride, 4,4-azobis-(4-cyanovaleric acid), etc. More various thermal polymerization initiators are well disclosed in 'Principle of Polymerization' written by Odian, (Wiley, 1981), p 203, however the example of the thermal polymerization initiator is not limited thereto.

The thermal polymerization initiator may be included at a concentration of about 0.001% by weight to about 0.5% by weight based on the monomer composition. When the concentration of the thermal polymerization initiator is too low, the additional thermal polymerization hardly occurs and effects obtained by the addition of the thermal polymerization initiator may be poor, and when the concentration of the thermal polymerization initiator is too high, the molecular weight of the superabsorbent polymer becomes small and the physical properties may become uneven.

In addition, the kind of the internal crosslinking agent included in the monomer composition is the same as described above. Such internal crosslinking agent may be included at a concentration of 0.01% by weight to about 0.5% by weight based on the monomer composition, thereby crosslinking the prepared polymer. Further, as described above, the internal crosslinking agent may be used in a ratio of 0.005 mol or more, 0.005 mol to 0.1 mol, or 0.005 mol to 0.05 mol (or 0.3 parts by weight or more, or 0.3 to 0.6 parts by weight relative to 100 parts by weight of acrylic acid), based on 1 mol of non-neutralized acrylic acid included in the monomer. As the internal crosslinking agent is used within the above content range, high gel strength of the base polymer powder may be suitably achieved and the superabsorbent polymer more suitably satisfying the above-described physical properties of one embodiment may be prepared.

In addition, the monomer composition may further include additives such as a thickener, a plasticizer, a preservation stabilizer, an antioxidant, etc., as needed.

The monomer composition may be prepared in the form of solution in which the raw materials such as the above-described water-soluble ethylene-based unsaturated monomer, photo-polymerization initiator, thermal polymerization initiator, internal crosslinking agent, and additives are dissolved in a solvent.

In this regard, as the solvent applicable, any solvent may be used without limitations in the constitution as long as it is able to dissolve the above raw materials. For example, one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide may be used in combination.

The solvent may be included in the residual quantity excluding the above-described components, based on the total content of the monomer composition.

Meanwhile, the method of preparing the water-containing gel polymer by subjecting the monomer composition to the thermal polymerization or photo-polymerization may be used without particular limitation in the constitution as long as it is a polymerization method that is generally used.

Specifically, the polymerization method is largely classified into thermal polymerization and photo-polymerization according to a polymerization energy source. Usually, the thermal polymerization may be carried out in a reactor like a kneader equipped with agitating spindles, and the photo-polymerization may be carried out in a reactor equipped with a movable conveyor belt. However, the polymerization methods disclosed above are only examples, and the present invention is not limited to the polymerization methods disclosed above.

As an example, the water-containing gel polymer, which is obtained by thermal polymerization in the reactor like the kneader equipped with agitating spindles disclosed above, by providing hot air thereto, or heating the reactor, may have a size of centimeters or millimeters when it is discharged from the outlet of the reactor, according to the types of the agitating spindles equipped in the reactor. Specifically, the size of the obtained water-containing gel polymer may vary according to a concentration of the monomer composition fed thereto, a feeding speed, etc., and a water-containing gel polymer having a weight average particle diameter of about 2 mm to 50 mm may be generally obtained.

Further, as described above, when the photo-polymerization is carried out in a reactor equipped with a movable conveyor belt, the water-containing gel polymer that is generally obtained may be a water-containing gel polymer of a sheet-type having a width of the belt. In this case, a thickness of the polymer sheet may vary according to the concentration of the monomer composition fed thereto and the feeding speed, but the monomer composition may be preferably fed such that a polymer sheet having a thickness of about 0.5 cm to about 5 cm may be obtained. If the monomer composition is fed such that the thickness of the sheet-type polymer becomes too thin, production efficiency becomes low, which is not preferred. If the thickness of the sheet-type polymer exceeds 5 cm, the polymerization reaction may not uniformly occur throughout the thickness of the polymer due to the excessively high thickness.

In this regard, the water-containing gel polymer thus obtained by the method may generally have a water content of about 40% by weight to about 80% by weight. Meanwhile, the term "water content", as used herein, means a water content in the total weight of the water-containing gel polymer, which is obtained by subtracting the weight of the dried polymer from the weight of the water-containing gel polymer. Specifically, the water content is defined as a value calculated by measuring the weight loss according to evaporation of water in the polymer during the drying process of increasing the temperature of the polymer with infrared heating. At this time, the water content is measured under the drying conditions which are determined as follows: the temperature is increased from room temperature to about 180 degrees Celsius, then the temperature is maintained at 180° C., and the total drying time is set to 20 minutes, including 5 minutes for the temperature rising step.

Next, the step of drying the water-containing gel polymer thus obtained is performed.

If necessary, a coarsely pulverizing step may be further performed before drying, in order to increase the efficiency of the drying step.

In this regard, a pulverizer used herein may include, but is not limited to, any one selected from the group consisting of a vertical pulverizer, a turbo cutter, a turbo grinder, a rotary cutter mill, a cutter mill, a disc mill, a shred crusher, a crusher, a chopper, and a disc cutter.

In this regard, the coarsely pulverizing step may be performed such that the water-containing gel polymer has a particle size of about 2 mm to 10 mm.

To pulverize the polymer to have a particle size of less than 2 mm is technically not easy due to a high water content of the water-containing gel polymer, and a phenomenon of agglomeration between the pulverized particles may occur. Meanwhile, if the polymer is pulverized to have a particle size of larger than 10 mm, the effect of increasing the efficiency in the subsequent drying step may be poor.

The water-containing gel polymer coarsely pulverized as above or immediately after polymerization without the coarsely pulverizing step is subjected to a drying step. At this time, a drying temperature of the drying step may be about 150° C. to about 250° C. When the drying temperature is lower than 150° C., there is a concern that the drying time becomes excessively long or the physical properties of the superabsorbent polymer finally formed may be deteriorated, and when the drying temperature is higher than 250° C., only the surface of the polymer is dried, and thus there is a concern that fine powder may be generated during the subsequent pulverization process and the physical properties of the superabsorbent polymer finally formed may be deteriorated. Therefore, the drying process may be preferably performed at a temperature of about 150° C. to about 200° C., and more preferably about 160° C. to about 180° C.

Meanwhile, the drying step may be carried out for about 20 min to about 90 min, in consideration of the process efficiency, but is not limited thereto.

Furthermore, any drying method may be selected and used in the drying step without limitation in the constitution as long as it may be generally used in the process of drying the water-containing gel polymer. Specifically, the drying step may be carried out by a method of supplying hot air, irradiating infrared rays, irradiating microwaves, irradiating ultraviolet rays, or the like. When the drying step as above is finished, the water content of the polymer may be about 0.1% by weight to about 10% by weight.

Next, the dried polymer obtained from the drying step is subjected to a pulverization step.

The polymer powder obtained from the pulverization step may have a particle size of about 150 µm to about 850 µm. Specific examples of a milling device that may be used to achieve the above particle size may include a pin mill, a hammer mill, a screw mill, a roll mill, a disc mill, a jog mill, or the like, but are not limited thereto.

In order to manage the physical properties of the superabsorbent polymer powder finally manufactured after the pulverization step, a separate size-sorting step may be performed according to the particle size of the polymer powder obtained after pulverization. Preferably, a polymer having a particle size of 150 µm to 850 µm is size-sorted and only particles having such particle size are subjected to the surface crosslinking reaction, and finally, is commercialized. The particle size distribution of the base polymer powder obtained through such process has been described above, and thus more specific description thereof will be omitted.

On the other hand, after obtaining the base polymer powder through the pulverizing and/or size-sorting processes, the superabsorbent polymer of an embodiment may be prepared through the surface-crosslinking process. A kind of the alumina particles applicable in the surface-crosslinking process has been described above, and thus a description thereof will be omitted.

The surface-crosslinking process may be performed by heat-treating the base polymer powder in the presence of the surface-crosslinking solution including the alumina particles and the surface-crosslinking agent in one embodiment, or by heat-treating the base polymer powder in the presence of the surface-crosslinking solution including the surface-crosslinking agent, after dry treatment of the base polymer powder with the alumina particles in a solid state, in another embodiment.

Of them, the method of another embodiment wherein the alumina particles are first subjected to dry treatment was confirmed to be more preferable than the method of the one embodiment, in terms of improvement of liquid permeability and absorption rate of the superabsorbent polymer, as supported by examples described below.

In the method according to one embodiment, to use the alumina particles which are suitably dispersed in the surface-crosslinking solution, particles having a contact angle of more than 10° and 50° or less (that is, alumina particles having relatively low hydrophobicity) may be used, or particles having a contact angle of 50° to 150° or less may be used together with a separate dispersing agent. As the dispersing agent, any dispersing agent which has been used to disperse alumina particles in a polar solvent such as an aqueous solvent may be used without limitation.

In the method of another embodiment wherein the alumina particles are first separately treated, the base polymer powder may be mixed with the alumina particles in a solid state to dry-treat the surface thereof. This treatment method may be performed according to a general dry treatment and/or mixing method of inorganic powder.

Further, the first alumina particles may be used in an amount of 0.001 to 1.0 parts by weight, or 0.01 to 0.2 parts by weight with respect to total 100 parts by weight of the base polymer. Therefore, liquid permeability and absorption rate of the superabsorbent polymer may be more effectively improved by using the first alumina particles.

There is no particular limitation in the method of adding the first alumina particles and surface-crosslinking agent or the surface-crosslinking solution including the surface-crosslinking agent to the base polymer powder. For example, a method of feeding the surface-crosslinking solution and the base polymer powder to the reactor and mixing them with each other, a method of spraying the surface-crosslinking solution to the base polymer powder, or a method of mixing the base polymer powder and the surface-crosslinking solution while continuously feeding them to a mixer being continuously operated may be used.

In the surface-crosslinking step, more suitable examples of the alkylene carbonate having 2 to 5 carbon atoms which is applicable as the surface-crosslinking agent may include ethylene carbonate, propylene carbonate, butylene carbonate, etc., and two or more selected therefrom may be used in combination. In addition, more suitable examples of a diol, triol, or polyol crosslinking agent containing an alkyl group having 2 to 12 carbon atoms or 2 to 10 carbon atoms or polyethylene glycol having 2 to 12 carbon atoms which is applicable as the surface-crosslinking agent may include 1,2-propanediol, 1,3-propanediol, glycerin, diethylene glycol, triethylene glycol, tetraethylene glycol, etc. Further, more suitable examples of a diepoxy, triepoxy, or polyepoxy crosslinking agent containing an alkyl group having 2 to 12 carbon atoms or polyethylene glycol having 2 to 12 carbon atoms may include diethylene glycol diglycidyl ether, triethylene glycol diglycidyl ether, ethylene glycol diglycidyl ether, etc.

Additionally, the surface-crosslinking solution may include water and/or methanol as a medium. As a result, there is an advantage that the surface-crosslinking agent and the first alumina particles are uniformly dispersed on the base polymer powder. In this regard, water and methanol may be applied by adjusting the addition rate with respect to 100 parts by weight of the base polymer powder for the purpose of inducing uniform dispersion of the surface-crosslinking agent and the first alumina particles, preventing agglomeration of the base polymer powder, and optimizing surface penetration depth of the surface-crosslinking agent at the same time.

Meanwhile, in the surface-crosslinking step, the surface crosslinking reaction may be allowed to occur by heating the surface crosslinking solution-added base polymer powder at a maximum reaction temperature of 140° C. to 210° C., or 150° C. to 200° C. for 5 min to 120 min, 10 min to 100 min, or 20 min to 80 min. More specifically, the surface crosslinking step may be performed by heat treatment as follows: an initial temperature of 20° C. to 130° C. or 40° C. to 120° C. is raised to the maximum reaction temperature for 10 min to 30 min, and the maximum reaction temperature is maintained for 5 min to 120 min.

The superabsorbent polymer suitably satisfying excellent liquid permeability and absorption rate may be prepared by satisfying conditions for the surface crosslinking process (particularly, the temperature-rising condition and reaction conditions at the maximum reaction temperature).

A means for raising the temperature for surface-crosslinking reaction is not particularly limited. Heating may be performed by providing a heating medium or by directly providing a heat source. In this case, a kind of the heating medium applicable herein may be a hot fluid such as steam, hot air, hot oil, etc., but is not limited thereto. The temperature of the heating medium provided may be suitably controlled, considering the means of the heating medium, the heating rate, and the target temperature. Meanwhile, as the heat source provided directly, an electric heater or a gas heater may be used, but the heat source is not limited to these examples.

Thereafter, the method of preparing the superabsorbent polymer according to the present invention may include the step of adding the second alumina particles to the surface-crosslinked base polymer powder and then mixing them with each other.

In general, a superabsorbent polymer has a hydrophilic surface, and irreversible agglomeration thereof may occur due to capillary force, hydrogen bonding, inter-particular diffusion, or inter-particular Van der Waals force, attributable to the presence of water between the particles upon drying after water absorption. Hence, water is essentially used in the course of polymerization and surface crosslinking of the superabsorbent polymer, and therefore agglomeration occurs, thereby increasing the internal load, ultimately incurring damage to the system. Furthermore, since the agglomerated superabsorbent polymer has a large particle size, which is unsuitable for use in practice, a disintegration process must be introduced in order to suitably decrease the large particle size. In addition, strong force is applied during the disintegration process, leading to undesirable deterioration of the physical properties of the superabsorbent polymer, due to attrition of the superabsorbent polymer.

In the present invention, the first alumina particles may be used at the time of surface-crosslinking to form a proper crosslinked structure, and at the same time, the second alumina particles defined by a predetermined range of contact angle may be treated immediately after surface-crosslinking, thereby obtaining an effect of more sufficiently preventing agglomeration.

First, in the preparation method of an embodiment, second alumina particles having a water contact angle of more than 10°, more than 10° and 150° or less, or more suitably, 12° to 150°, may be used at the time of surface-crosslinking.

As a result, the superabsorbent polymer prepared by the method of an embodiment may further include the second alumina particles which are dispersed on the surface of the surface-crosslinked polymer powder.

In the step of adding the second alumina particles to the surface-crosslinked superabsorbent polymer and mixing them with each other, the second alumina particles may be preferably added in an amount of 0.01 to 1.0 parts by weight or 0.05 to 0.3 parts by weight with respect to 100 parts by weight of the surface-crosslinked superabsorbent polymer. If the content of the second alumina particles is smaller than the above range, the effect of preventing agglomeration of the superabsorbent polymer is unsatisfactory, and if the content of the second alumina particles is larger than the above range, processibility of the polymer may decrease. Further, in the step of mixing the second alumina particles, a mixing speed after adding the second alumina particles to the surface-crosslinked water-containing gel polymer is preferably 200 rpm to 3000 rpm. If the mixing speed is lower than 200 rpm, the mixing effect is unsatisfactory, and if the mixing rate is higher than 3000 rpm, there is a problem of excessive pulverization. Further, in the step of mixing the second alumina particles, a method of or an apparatus for adding the second alumina particles to the surface-crosslinked water-containing gel polymer and mixing them with each other is not particularly limited, as long as it is used in the same art. Further, in the step of mixing the second alumina particles, a mixing time after adding the second alumina particles to the surface-crosslinked water-containing gel polymer is preferably 2 s to 3 min. If the mixing time is shorter than 2 s, the mixing effect is unsatisfactory, and if the mixing time is longer than 3 min, there is a problem of excessive pulverization.

Meanwhile, the superabsorbent polymer prepared by the above-described method may have centrifuge retention capacity (CRC) of 25 g/g to 35 g/g, or 26.5 g/g to 32 g/g. As such, the superabsorbent polymer of an embodiment may exhibit excellent absorbency under no load.

In this regard, centrifuge retention capacity (CRC) for a physiological saline solution may be calculated by the following Calculation Equation 1 after soaking the superabsorbent polymer in a physiological saline solution over a period of 30 min.

$$CRC(g/g)=\{[W_2(g)-W_1(g)-W_0(g)]/W_0(g)\}$$ [Calculation Equation 1]

Herein, $W_0(g)$ is an initial weight (g) of the superabsorbent polymer, $W_1(g)$ is a weight of an apparatus not including the superabsorbent polymer, which is measured after soaking the same in a physiological saline solution for 30 min and then draining water off using a centrifuge at 250 G for 3 min, and $W_2(g)$ is the weight of the apparatus including the superabsorbent polymer, which is measured after soaking the superabsorbent polymer in a physiological saline solution at room temperature for 30 min, and then draining water off using a centrifuge at 250 G for 3 min.

Further, the superabsorbent polymer may have absorbency under pressure (AUP) of 24 g/g to 30 g/g, or 24.2 g/g to 26 g/g. As such, the superabsorbent polymer of an embodiment may exhibit excellent absorbency even under pressure.

The absorbency under pressure (AUP) may be calculated by the following Calculation Equation 2 after soaking the superabsorbent polymer in a physiological saline solution under a pressure of 0.7 psi over a period of 1 hour (h).

$$AUP(g/g)=[W_4(g)-W_3(g)]/W_0(g)$$ [Calculation Equation 2]

Herein, $W_0(g)$ is an initial weight (g) of the superabsorbent polymer, $W_3(g)$ is the total sum of a weight of the superabsorbent polymer and a weight of the apparatus capable of providing a load for the superabsorbent polymer, and $W_4(g)$ is the total sum of a weight of the superabsorbent polymer and a weight of the apparatus capable of providing a load to the superabsorbent polymer, after soaking the superabsorbent polymer in a physiological saline solution under a load (0.7 psi) for 1 h.

In addition, the superabsorbent polymer according to the present invention may have a vortex time of 35 seconds or less, or 20 s to 35 s, absorbency under load (0.3Gel-vac.) of 20 g/g or more, or 20 to 22 g/g, gel bed permeability (GBP) of 45 Darcy or more, or 40 Darcy to 85 Darcy, and absorbency under pressure (0.9AUL) of 19.5 g/g or more, or 19.5 g/g to 25 g/g.

The superabsorbent polymer obtained by the above-described preparation method may maintain excellent absorption performance such as centrifuge retention capacity, absorbency under pressure, etc., and may satisfy more improved liquid permeability, absorption rate, etc. Therefore, the superabsorbent polymer may be suitably applied to hygiene products such as diapers, especially ultra-thin diapers with reduced pulp content.

Hereinafter, preferred examples of the present invention will be described in detail. However, these examples are for illustrative purposes only, and the scope of the present invention is not intended to be limited by these examples.

EXAMPLES

Example 1

500 g of acrylic acid, 1.05 g of polyethylene glycol diacrylate (Mw=523) as a crosslinking agent, 0.69 g of trimethylol propane triacrylate containing 9 mol % ethylene oxide, and 0.04 g of IRGACURE 819 as a photoinitiator were mixed. Subsequently, 860 g of 24% caustic soda (NaOH) was mixed therewith to prepare a neutralized monomer aqueous solution.

During neutralization of the monomer aqueous solution, heat of neutralization of about 70° C. was generated. The temperature of the neutralization solution was cooled to about 40° C., and then the neutralization solution was mixed with 55 g of an aqueous solution containing 1.02 g of sodium persulfate as a thermal initiator, 0.03 g of S1670 as a surfactant, and 1.02 g of sodium bicarbonate as a foaming agent.

The prepared mixed solution was poured into a vat-type tray installed in a square polymerizer which had a light irradiation device installed at the top and was preheated to 80° C. Thereafter, the mixed solution was subjected to light irradiation. At about 25 s after light irradiation, it was observed that a gel was generated from the surface, and at 35 s after light irradiation, bubble formation occurred. Then, polymerization reaction was allowed to continue for an additional 2 min, and the polymerized sheet was taken and cut in a size of 5 cm×5 cm The cut sheet was subjected to a chopping process using a meat chopper to prepare crumbs.

Subsequently, the water-containing gel polymer was dried with a hot air dryer at 180° C. for 30 min, and the dried water-containing gel polymer was pulverized with a pin mill pulverizer. Next, the polymer was size-sorted into a polymer having a particle size of less than 150 μm and a polymer having a particle size of 150 μm to 850 μm by using a sieve.

A surface treatment solution containing 0.2 g (0.1 parts by weight) of Aeroxide Alu 130 as first alumina particles, 0.8 g (0.4 parts by weight) of allyl methacrylate, 6.0 g (3.0 parts by weight) of water as a solvent, and 7.0 g (3.5 parts by weight) of methanol was prepared. The surface-crosslinking solution was sprayed on 200 g of the base polymer powder and mixed under stirring at room temperature such that the surface treatment solution was evenly distributed on the base polymer powder. Thereafter, the base polymer powder was added to a surface crosslinking reactor and subjected to a surface crosslinking reaction.

In the surface crosslinking reactor, the base polymer powder was confirmed to be gradually heated to an initial temperature of around 80° C., and after passage of about 15 min, the reactor was operated to reach a maximum reaction temperature of 190° C. After reaching this maximum reaction temperature, an additional reaction was carried out for 40 min and then a superabsorbent polymer sample finally produced was taken. After the surface crosslinking process, 100 g of the surface-crosslinked superabsorbent polymer was mixed with 0.1 g (0.1 parts by weight) of Aeroxide Alu 130 as second alumina particles at 1000 rpm for 60 s. Thereafter, the resulting mixture was screened using a sieve to obtain a surface-crosslinked superabsorbent polymer with a particle size of about 150 μm to 850 μm.

The Aeroxide Alu 130 used above had a particle size of 5 μm, a BET specific surface area of 700 $m^2/g$, and a water contact angle of 144°. The measurement of the particle size of the Aeroxide Alu 130 was conducted according to ISO 13320. HELOS (Helium-Neon Laser Optical [0086] System) was used to analyze the particle size by high-speed non-variable laser diffraction. The BET specific surface area and porosity were determined by using a BET analyzer. The measurement of the water contact angle was conducted by using a contact angle analyzer (KRUSS DSA100). Specifically, double-sided tape was attached on a flat glass plate. Thereafter, the fine particles were coated thereon in the form of a monolayer. Subsequently, 5 μl of ultra-pure water was deposited in a drop form over the monolayer, and then an angle value between the water drop and the glass plate was measured four times and an average value was calculated.

Example 2

A superabsorbent polymer was obtained in the same manner as in Example 1, except that after reaching the maximum reaction temperature of 190° C., reaction was further allowed for 45 min.

Example 3

A superabsorbent polymer was obtained in the same manner as in Example 1, except that the second alumina was used in an amount of 0.08 g (0.08 wt %).

Example 4

A superabsorbent polymer was obtained in the same manner as in Example 1, except that the second alumina was used in an amount of 0.12 g (0.12 wt %).

Comparative Example 1

A superabsorbent polymer was obtained in the same manner as in Example 1, except that 0.1 g (0.1 wt %) of hydrophobic silica particles of Aerosil 380 was used instead of the second alumina particles.

Comparative Example 2

A superabsorbent polymer was obtained in the same manner as in Example 1, except that 0.1 g (0.1 wt %) of hydrophobic silica particles of Aerosil 380 was used instead of the first alumina particles.

Comparative Example 3

A superabsorbent polymer was obtained in the same manner as in Example 1, except that 0.2 g (0.1 wt %) of hydrophobic silica particles of Aerosil 380 was used instead of the first alumina particles and 0.1 g (0.1 wt %) of hydrophobic silica particles of Aerosil 380 was used instead of the second alumina particles.

Comparative Example 4

A superabsorbent polymer was obtained in the same manner as in Example 1, except that the second alumina particles were not used.

Comparative Example 5

A superabsorbent polymer was obtained in the same manner as in Example 1, except that the first alumina particles were not used.

Comparative Example 6

A superabsorbent polymer was obtained in the same manner as in Comparative Example 3, except that the second alumina particles were not used.

Comparative Example 7

A superabsorbent polymer was obtained in the same manner as in Comparative Example 3, except that the first alumina particles were not used.

Comparative Example 8

A superabsorbent polymer was obtained in the same manner as in Example 1, except that the first and second alumina particles were not used.

Specific components and contents of the inorganic materials used at the time of surface-crosslinking and immediately after surface-crosslinking during the process of preparing the superabsorbent polymer in Examples 1 to 4 and Comparative Examples 1 to 8 are as shown in the following Table 1.

TABLE 1

| | At the time of surface-crosslinking | | | Immediately after surface-crosslinking | | | Additional surface crosslinking reaction time at |
|---|---|---|---|---|---|---|---|
| | Inorganic material | Product name | Addition amount (%) | Inorganic material | Product name | Addition amount (%) | maximum temperature (min) |
| Example 1 | alumina | Aeroxide Alu 130 | 0.1 | alumina | Aeroxide Alu 130 | 0.1 | 40 |
| Example 2 | alumina | Aeroxide Alu 130 | 0.1 | alumina | Aeroxide Alu 130 | 0.1 | 45 |
| Example 3 | alumina | Aeroxide Alu 130 | 0.1 | alumina | Aeroxide Alu 130 | 0.08 | 40 |
| Example 4 | alumina | Aeroxide Alu 130 | 0.1 | alumina | Aeroxide Alu 130 | 0.12 | 40 |
| Comparative Example 1 | alumina | Aeroxide Alu 130 | 0.1 | silica | Aerosil 380 | 0.1 | 40 |
| Comparative Example 2 | silica | Aerosil 380 | 0.1 | alumina | Aeroxide Alu 130 | 0.1 | 40 |
| Comparative Example 3 | silica | Aerosil 380 | 0.1 | silica | Aerosil 380 | 0.1 | 40 |
| Comparative Example 4 | alumina | Aeroxide Alu 130 | 0.1 | — | — | — | 40 |
| Comparative Example 5 | — | — | — | alumina | Aeroxide Alu 130 | 0.1 | — |
| Comparative Example 6 | silica | Aerosil 380 | 0.1 | — | — | — | 40 |
| Comparative Example 7 | — | — | — | silica | Aerosil 380 | 0.1 | — |
| Comparative Example 8 | — | — | — | — | — | — | — |

Experimental Example

Physical properties such as CRC, Vortex, 0.9AUL, 0.3Gel-vac., GBP, etc., of the respective superabsorbent polymers of Examples 1 to 4 and Comparative Examples 1 to 8 were measured and evaluated by the following methods.

(1) Evaluation of Particle Size

The particle sizes of the base polymer powder and the superabsorbent polymer used in the examples and comparative examples were measured in accordance with the European Disposables and Nonwovens Association (EDANA) standard test method WSP 220.3.

(2) Centrifuge Retention Capacity (CRC)

With regard to the superabsorbent polymers of the examples and comparative examples, centrifuge retention capacity (CRC) by absorbency under no load was measured in accordance with the European Disposables and Nonwovens Association (EDANA) standard test method WSP 241.3.

That is, each polymer $W_0(g)$ (about 2.0 g) of the examples and comparative examples was uniformly placed into a nonwoven-fabric-made bag, followed by sealing. Then, the bag was immersed in a physiological saline solution composed of 0.9% by weight of aqueous sodium chloride at room temperature. 30 min later, the bag was drained at 250 G for 3 min with a centrifuge, and the weight $W_2(g)$ of the bag was then measured. The same procedure was carried out using no polymer, and the resultant weight $W_1(g)$ was measured.

From these weights thus obtained, CRC (g/g) was calculated according to Calculation Equation 1 to confirm centrifuge retention capacity.

$$CRC(g/g)=\{[W_2(g)-W_1(g)-W_0(g)]/W_0(g)\} \quad \text{[Calculation Equation 1]}$$

Herein, $W_0(g)$ is an initial weight (g) of the superabsorbent polymer, $W_1(g)$ is a weight of an apparatus not including the superabsorbent polymer, which is measured after soaking the same in a physiological saline solution for 30 min and then draining water off using a centrifuge at 250 G for 3 min, and $W_2(g)$ is the weight of the apparatus including the superabsorbent polymer, which is measured after soaking the superabsorbent polymer in a physiological saline solution at room temperature for 30 min, and then draining water off using a centrifuge at 250 G for 3 min.

(3) Absorbing Under Pressure (AUP)

With regard to the superabsorbent polymers of the examples and comparative examples, absorbency under pressure (AUP) was measured in accordance with the European Disposables and Nonwovens Association (EDANA) standard test method WSP 242.3.

First, a 400 mesh stainless steel net was installed in the bottom of a plastic cylinder having an internal diameter of 60 mm. Each superabsorbent polymer $W_0$ (0.90 g) of Examples 1 to 4 and Comparative Examples 1 to 8 was uniformly scattered on the steel net at a temperature of 23±2° C. and relative humidity of 45%, and a piston which could uniformly provide a load of 4.83 kPa (0.7 psi) was put thereon, in which the external diameter of the piston was slightly smaller than 60 mm such that there was substantially no gap between the internal wall of the cylinder and the piston, and vertical movement of the cylinder was not interrupted. At this time, the weight $W_3(g)$ of the apparatus was measured.

After putting a glass filter having a diameter of 125 mm and a thickness of 5 mm in a Petri dish having a diameter of 150 mm, a physiological saline solution composed of 0.90% by weight of sodium chloride was poured in the dish until the surface level became equal to the upper surface of the glass filter. A sheet of filter paper having a diameter of 120 mm was put thereon. The measuring apparatus was put on the filter paper and the solution was absorbed for 1 h under load. After 1 h, the weight $W_4(g)$ was measured after lifting the measuring apparatus up.

Each weight thus obtained was used to calculate AUP (g/g) according to the following Calculation Equation 2 to confirm absorbency under pressure.

$$AUP(g/g)=[W_4(g)-W_3(g)]/W_0(g) \quad \text{[Calculation Equation 2]}$$

Herein, $W_0(g)$ is an initial weight (g) of the superabsorbent polymer, $W_3(g)$ is the total sum of a weight of the superabsorbent polymer and a weight of the apparatus capable of providing a load for the superabsorbent polymer, and $W_4(g)$ is the total sum of a weight of the superabsorbent polymer and a weight of the apparatus capable of providing a load to the superabsorbent polymer, after soaking the superabsorbent polymer in a physiological saline solution under a load (0.7 psi) for 1 h.

(4) Absorption Rate (Vortex)

The absorption rate of the superabsorbent polymer was determined in seconds by measuring a time which was required until the vortex disappears, after adding 2 g of the superabsorbent polymer to 50 mL of a physiological saline solution and then agitating it at 600 rpm.

(5) Absorbency Under Load (0.9AUL)

Absorbency under load (AUL) of 0.9 psi in the physiological saline solution was measured according to EDANA WSP 242.2.

In detail, a 400 mesh stainless steel screen was installed in the bottom of the plastic cylinder having an internal diameter of 25 mm. The superabsorbent polymer $W_0$ (0.16 g) to be tested for absorbency under pressure was uniformly scattered on the screen at room temperature and humidity of 50%. Subsequently, a piston which could uniformly provide a load of 6.3 kPa (0.9 psi) was put thereon, in which an external diameter of the piston was slightly smaller than 25 mm such that there was substantially no gap between the internal wall of the cylinder and the piston, and vertical movement of the cylinder was not interrupted. Then, a weight $W_5(g)$ of the prepared apparatus was measured. After putting a glass filter having a diameter of 90 mm and a thickness of 5 mm in a Petri dish having a diameter of 150 mm, 0.9% by weight of a physiological saline solution was poured in the Petri dish until the surface level became equal to the upper surface of the glass filter. A sheet of filter paper having a diameter of 90 mm was put thereon. The apparatus was put on the filter paper, and the superabsorbent polymer in the apparatus was allowed to swell by the physiological saline solution under a load. 1 h later, the weight $W_6(g)$ of the apparatus containing the swollen superabsorbent polymer was measured.

The weights thus measured were used to calculate absorbency under pressure according to the following Calculation Equation 3.

$$AUL(g/g)=[W_6(g)-W_5(g)]/W_0(g) \quad \text{[Calculation Equation 3]}$$

Herein $W_0(g)$ is an initial weight (g) of the superabsorbent polymer, $W_5(g)$ is the total sum of the weight of the superabsorbent polymer and the weight of the apparatus capable of providing a load for the superabsorbent polymer, and $W_6(g)$ is the total sum of the weight of the superabsorbent polymer after soaking the superabsorbent polymer in the physiological saline solution under a load (0.9 psi) for 1 h, and the weight of the apparatus capable of providing a load for the superabsorbent polymer.

(6) 5 Min 0.3 Gel-Vacuum AUL

A 400 mesh stainless steel screen was installed in the bottom of the plastic cylinder having an internal diameter of 25 mm. The superabsorbent polymer $W_0$ to be tested for 5 min Gel-Vacuum AUL was uniformly scattered on the screen at room temperature and humidity of 50%. Subsequently, a piston which could uniformly provide a load of 0.3 psi was put thereon, in which an external diameter of the piston was slightly smaller than 25 mm such that there was substantially no gap between the internal wall of the cylinder and the piston, and the vertical movement of the cylinder was not interrupted. Then, a weight $W_7(g)$ of the prepared apparatus was measured. After putting a glass filter having a diameter of 90 mm and a thickness of 5 mm in a Petri dish having a diameter of 150 mm, 0.9% by weight of a physiological saline solution was poured in the Petri dish until the surface level became equal to the upper surface of the glass filter. A sheet of filter paper having a diameter of 90 mm was put thereon. Subsequently, the apparatus was put on the filter paper, and the superabsorbent polymer in the apparatus was allowed to swell by the physiological saline solution under a load. 5 min later, residual liquid was removed by using a vacuum pump. At this time, residual liquid not absorbed between the swollen superabsorbent polymer particles was removed. Then, the weight $W_8(g)$ of the apparatus containing the superabsorbent polymer was measured. The weights thus measured were used to calculate 5 min Gel-Vacuum AUL according to the following Calculation Equation 4.

$$5 \text{ min Gel-Vacuum AUL}(g/g)=[W_8(g)-W_7(g)]/W_0(g) \qquad \text{[Calculation Equation 4]}$$

Herein, $W_0(g)$ is an initial weight (g) of the superabsorbent polymer, $W_7(g)$ is the total sum of the weight of the superabsorbent polymer and the weight of the apparatus capable of providing a load for the superabsorbent polymer, and $W_8(g)$ is the sum of the weight of the superabsorbent polymer which is measured after soaking the superabsorbent polymer in the physiological saline solution under a load (0.3 psi) for 5 min and removing residual liquid using a vacuum pump, and the weight of the apparatus capable of providing a load for the superabsorbent polymer.

(7) Gel Bed Permeability (GBP)

Free swell gel bed permeability (GBP) in a physiological saline solution was measured according to the following method described in Korean Patent Application. No. 10-2014-7018005.

In detail, an apparatus illustrated in FIGS. 1 to 3 was used to conduct a free swell GBP test. First, a plunger 536 with a weight 548 seated thereon was placed in an empty sample container 530, and the height from the top of the weight 548 to the bottom of the sample container 530 was measured using a suitable gauge accurate to 0.01 mm. The force the thickness gauge applies during measurement was controlled to less than about 0.74 N.

Meanwhile, among the superabsorbent polymers to be tested for GBP, superabsorbent polymers, which were passed through a US standard 30 mesh screen and retained on a US standard 50 mesh screen, were selected to obtain the superabsorbent polymer having a particle size of 300 μm to 600 μm.

About 2.0 g of the size-sorted superabsorbent polymer was placed in a sample container 530 and spread out evenly on the bottom of the sample container. This container without the plunger 536 and weight 548 therein was then submerged in a 0.9% by weight physiological saline solution for about 60 min to allow the superabsorbent polymer to swell free of any restraining load. At this time, the sample container 530 was set on a mesh located in a liquid reservoir such that the sample container 530 was raised slightly above the bottom of the liquid reservoir. The mesh did not inhibit the flow of the physiological saline solution into the sample container 530. During saturation, a depth of the physiological saline solution was controlled such that the surface within the sample container was defined solely by the swollen superabsorbent polymer, rather than the physiological saline solution.

At the end of this period, the plunger 536 and weight 548 assembly was placed on the swollen superabsorbent polymer 568 in the sample container 530 and then the sample container 530, plunger 536, weight 548, and swollen superabsorbent polymer 568 were removed from the solution. Then, before GBP measurement, the sample container 530, plunger 536, weight 548, and swollen superabsorbent polymer 568 were allowed to remain at rest for about 30 s on a large grid non-deformable plate of uniform thickness. The height from the bottom of the weight 548 to the top of the sample container 530 was measured again by using the same thickness gauge that was used previously. The height measurement of the apparatus where the plunger 536 and the weight 548 were placed in the empty sample container 530 was subtracted from the height measurement of the apparatus containing the swollen superabsorbent polymer 568 to obtain the thickness or height "H" of the swollen superabsorbent polymer.

For GBP measurement, a flow of 0.9% physiological saline solution was delivered into the sample container 530 with the swollen superabsorbent polymer 568, the plunger 536, and the weight 548 inside. The flow rate of the physiological saline solution into the container 530 was adjusted to cause the physiological saline solution to overflow the top of the cylinder 534, resulting in a consistent head pressure equal to the height of the sample container 530. The quantity of solution passing through the swollen superabsorbent polymer 568 versus time was measured gravimetrically using a scale 602 and a beaker 603. Data points from the scale 602 were collected every second for at least 60 s once the overflow began. The flow rate Q through the swollen superabsorbent polymer 568 was determined in units of g/s by a linear least-squares fit of fluid (g) passing through the swollen superabsorbent polymer 568 versus time (s).

GBP ($cm^2$) was calculated from the obtained data according to the following Calculation Equation 5.

$$K=[Q \times H \times p]/[A \times \rho \times P] \qquad \text{[Calculation Equation 5]}$$

Herein K is gel bed permeability ($cm^2$),

Q is a flow rate (g/s),

H is a height of swollen superabsorbent polymer (cm),

μ is liquid viscosity (P) (about 1 cp for the physiological saline solution used in this test), A is a cross-sectional area for liquid flow (28.27 $cm^2$ for the sample container used in this test), ρ is a liquid density ($g/cm^3$) (about 1 $g/cm^3$ for the physiological solution used in this test), and P is a hydrostatic pressure ($dyne/cm^2$) (normally about 7797 $dyne cm^2$).

The hydrostatic pressure is calculated from $P=\rho \times g \times h$, wherein ρ is a liquid density ($g/cm^3$), g is gravitational acceleration (nominally 981 cm/s$^2$), and h is a fluid height (e.g., 7.95 cm for the GBP test described herein).

At least two samples were tested, and an average of the results was determined as free swell GBP of the superabsorbent polymer, and the unit was converted to Darcys (1 Darcy=0.98692×10$^{-8}$ cm$^2$).

The values of physical properties measured for the superabsorbent polymers of Examples 1 to 4 Comparative Examples 1 to 8 are shown in the following Table 2.

TABLE 2

|  | CRC (g/g) | Vortex (s) | 0.9 AUL (g/g) | 0.3 Gel-vac. (g/g) | GBP (Darcy) |
|---|---|---|---|---|---|
| Example 1 | 30.8 | 35 | 19.8 | 20.3 | 74 |
| Example 2 | 30.4 | 30 | 20.8 | 20.0 | 84 |
| Example 3 | 30.2 | 32 | 21.1 | 20.8 | 60 |
| Example 4 | 29.8 | 32 | 21.2 | 20.4 | 73 |
| Comparative Example 1 | 30.5 | 43 | 19.7 | 19.8 | 63 |
| Comparative Example 2 | 30.2 | 38 | 18.9 | 20.2 | 60 |
| Comparative Example 3 | 30.5 | 39 | 17.2 | 20.4 | 57 |
| Comparative Example 4 | 30.5 | 45 | 22.3 | 21.0 | 24 |
| Comparative Example 5 | 30.5 | 42 | 20.1 | 20.9 | 44 |
| Comparative Example 6 | 30.5 | 44 | 20.7 | 21.4 | 29 |
| Comparative Example 7 | 30.4 | 42 | 19.8 | 20.0 | 36 |
| Comparative Example 8 | 30.5 | 50 | 24 | 18.9 | 13 |

As shown in Table 2, it can be seen that when superabsorbent polymers are prepared by using specific alumina particles at the time of surface-crosslinking and immediately after surface-crosslinking according to the present invention, they may maintain excellent absorption performance such as centrifuge retention capacity, absorbency under pressure, etc., and may obtain more improved liquid permeability, absorption rate, etc. In particular, the superabsorbent polymers of Examples 1 to 4 were found to show remarkable improvement including centrifuge retention capacity (CRC) of 29.8 g/g to 30.8 g/g and absorbency under pressure (0.9AUL) of 19.8 g/g to 21.2 g/g, and absorption rate (vortex) of 30 s to 35 s, absorbency under pressure (0.3Gel-vac.) of 20.0 g/g or more, or 20.0 to 20.8 g/g, and gel bed permeability (GBP) of 60 Darcy to 84 Darcy.

In contrast, the superabsorbent polymers of Comparative Examples 1 to 8, which were prepared by using one kind of alumina particles or silica particles according to the known methods showed reduction in absorption performance such as centrifuge retention capacity, absorbency under pressure, etc., or remarkable reduction in liquid permeability, prevention of agglomeration, or absorption rate.

The invention claimed is:

1. A method of preparing a superabsorbent polymer, the method comprising the steps of:
performing crosslinking polymerization of water-soluble ethylene-based unsaturated monomers having acidic groups which are at least partially neutralized in the presence of an internal crosslinking agent to form a water-containing gel polymer including a crosslinked polymer;
drying, pulverizing, and size-sorting the water-containing gel polymer to form a base polymer powder;
performing surface-crosslinking of the base polymer powder using a surface-crosslinking solution including one or more surface-crosslinking agents selected from the group consisting of an alkylene carbonate having 2 to 5 carbon atoms, diol, triol, or polyol containing an alkyl group having 2 to 12 carbon atoms or polyethylene glycol having 2 to 12 carbon atoms, and diepoxy, triepoxy, or polyepoxy containing an alkyl group having 2 to 12 carbon atoms or polyethylene glycol having 2 to 12 carbon atoms, in the presence of first alumina particles; and
adding second alumina particles to the surface-crosslinked base polymer powder and then mixing them with each other,
wherein the first alumina is included in an amount of 0.01 to 0.2 parts by weight with respect to 100 parts by weight of the base polymer powder, and the second alumina is included in an amount of 0.05 to 0.3 parts by weight with respect to 100 parts by weight of the surface-crosslinked superabsorbent polymer powder.

2. The method of preparing the superabsorbent polymer of claim 1, wherein the surface-crosslinking step includes the step of surface-crosslinking the base polymer powder by heat treatment in the presence of the surface-crosslinking solution including the first alumina particles and the surface-crosslinking agent.

3. The method of preparing the superabsorbent polymer of claim 1, wherein the surface-crosslinking step includes the steps of treating the base polymer powder with the first alumina particles in a solid state, and
surface-crosslinking the base polymer powder by heat treatment in the presence of the surface-crosslinking solution including the surface-crosslinking agent.

4. The method of preparing the superabsorbent polymer of claim 1, wherein the first alumina particles have a water contact angle of 10° to 150°.

5. The method of preparing the superabsorbent polymer of claim 1, wherein the water-soluble ethylene-based unsaturated monomer includes one or more selected from the group consisting of an anionic monomer or salts thereof, a nonionic hydrophilic monomer, and an amino group-containing unsaturated monomer or a quaternary compound thereof, and in which the anionic monomer is acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid; the nonionic hydrophilic monomer is (meth)acrylamide, N-substituted (meth)acrylate, 2-hydroxyethyl (meth)acrylate, 2-hydroxypropyl(meth)acrylate, methoxy polyethylene glycol (meth)acrylate, or polyethylene glycol (meth)acrylate; and the amino group-containing unsaturated monomer is (N,N)-dimethylaminoethyl(meth)acrylate or (N,N)-dimethylaminopropyl(meth)acrylate.

6. The method of preparing the superabsorbent polymer of claim 1, wherein the internal crosslinking agent includes one or more selected from the group consisting of bis(meth)acrylamide containing an alkyl group having 2 to 12 carbon atoms or polyethylene glycol having 2 to 12 carbon atoms, a poly(meth)acrylate of polyol containing an alkyl group having 2 to 12 carbon atoms or polyethylene glycol having 2 to 12 carbon atoms, and a poly(meth)allyl ether of polyol containing an alkyl group having 2 to 12 carbon atoms or polyethylene glycol having 2 to 12 carbon atoms.

7. The method of preparing the superabsorbent polymer of claim 1, wherein the base polymer powder is pulverized and size-sorted such that it has a particle size of 150 μm to 850 μm.

8. The method of preparing the superabsorbent polymer of claim 1, wherein the surface-crosslinking step is performed by heat treatment by raising an initial temperature of 20° C. to 130° C. to a maximum temperature of 140° C. to 200° C. for 10 min to 30 min and maintaining the maximum temperature for 5 min to 60 min.

9. The method of preparing the superabsorbent polymer of claim 1, wherein the second alumina particles have a water contact angle of 10° to 150°.

10. The method of preparing the superabsorbent polymer of claim 1, wherein mixing of the second alumina particles is performed at a speed of 100 to 3000 rpm.

11. The method of preparing the superabsorbent polymer of claim 1, wherein mixing of the second alumina particles is performed for 2 s to 3 min.

12. The method of preparing the superabsorbent polymer of claim 1, wherein the first alumina is included in an amount of 0.1 by weight with respect to 100 parts by weight of the base polymer powder, and the second alumina is included in an amount of 0.08 to 0.12 parts by weight with respect to 100 parts by weight of the surface-crosslinked superabsorbent polymer powder.

* * * * *